United States Patent [19]

Strupczewski et al.

[11] 4,352,811

[45] Oct. 5, 1982

[54] 3-(1-SUBSTITUTED-4-PIPERIDYL)-1,2-BENZISOXAZOLES

[75] Inventors: Joseph T. Strupczewski; Richard C. Allen, both of Flemington, N.J.

[73] Assignee: Hoechst-Roussel Pharmaceuticals Inc., Somerville, N.J.

[21] Appl. No.: 319,872

[22] Filed: Nov. 12, 1981

[51] Int. Cl.[3] .............. A61K 31/445; C07D 413/04; C07D 413/14
[52] U.S. Cl. .................................... 424/267; 546/198
[58] Field of Search .................. 546/198; 424/267

[56] References Cited

U.S. PATENT DOCUMENTS 3,678,062  7/1972  Bauer et al. .................... 424/263
4,217,349  8/1980  Katsube et al. ................ 546/198

FOREIGN PATENT DOCUMENTS 51-136666  11/1976  Japan .............................. 546/198

OTHER PUBLICATIONS

Chemical Abstracts, vol. 79, item 137159j, (1973) abstracting German Offelegungsschrift 2,313,256, Sep. 20, (1973).

*Primary Examiner*—Robert T. Bond
*Attorney, Agent, or Firm*—Raymond R. Wittekind

[57] ABSTRACT

Novel 3-(1-substituted-4-piperidyl)-1,2-benzisoxazoles, processes for the preparation thereof, and methods of treating psychoses employing compounds and compositions thereof are disclosed.

49 Claims, No Drawings

3-(1-SUBSTITUTED-4-PIPERIDYL)-1,2-BENZISOXAZOLES

DESCRIPTION OF THE INVENTION

The present invention relates to novel piperidylbenzisoxazoles. More particularly, the present invention relates to 3-(1-substituted-4-piperidyl)-1,2-benzisoxazoles of formula 1

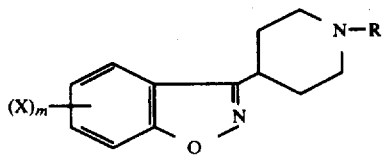

wherein R is a group of the formula

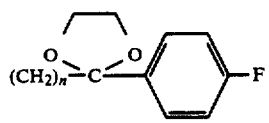

wherein n is 2 or 3; a group of the formula

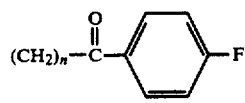

wherein n is 2 or 3; a group of the formula

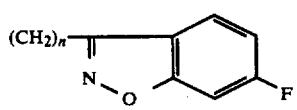

wherein n is 2 or 3; a group of the formula

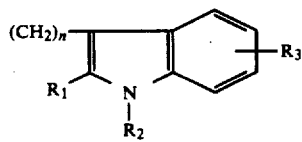

$R_1$ and $R_2$ are each independently hydrogen or loweralkyl, $R_3$ is hydrogen, halogen or loweralkyl, and n is 2 or 3; a group of the formula

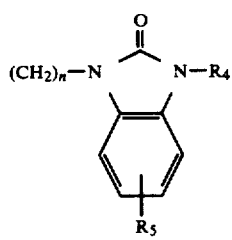

wherein $R_4$ is hydrogen or loweralkyl, $R_5$ is hydrogen, halogen or loweralkyl and n is 2 or 3; and a group of the formula

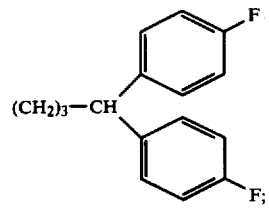

X is hydrogen, halogen, loweralkyl, loweralkoxy or hydroxy; and m is 1 or 2; the optical antipodes thereof; or pharmaceutically acceptable acid addition salts thereof which are useful for treating psychoses alone or in combination with inert psychoses-treating adjuvants.

Subgeneric to the 3-(1-substituted-4-piperidyl)-1,2-benzisoxazoles of the present invention are those compounds wherein:

(a) R is a group of the formula

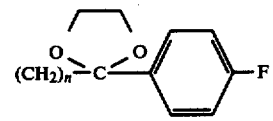

wherein n is as above;

(b) R is a group of the formula

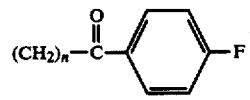

wherein n is as above;

(c) R is a group of the formula

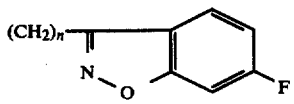

wherein n is as above;

(d) R is a group of the formula

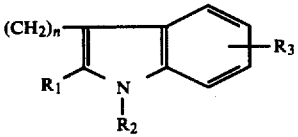

wherein $R_1$, $R_2$, $R_3$ and n are as above;

(e) R is a group of the formula

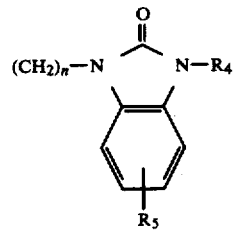

wherein R4, R5 and n are as above; and
(f) R is a group of the formula

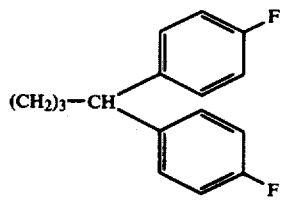

As used through the specification and appended claims, the term "alkyl" refers to a straight or branched chain hydrocarbon radical containing no unsaturation and having 1 to 10 carbon atoms such as methyl, ethyl, 1-propyl, 2-propyl, 1-butyl, 1-pentyl, 2-pentyl, 3-hexyl, 4-heptyl, 2-octyl, 3-nonyl, 4-decyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy, 2-methyloctoxy, octoxy, decoxy and the like; the term "alkanol" refers to a compound formed by a combination of an alkyl group and hydroxy radical. Examples of alkanols are methanol, ethanol, 1- and 2-propanol, 2,2-dimethylethanol, hexanol, octanol, decanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid and the like; the term "halogen" refers to a member of the family consisting of fluorine, bromine or iodine. The term "alkanone" refers to a compound formed by the combination of a carbonyl group and two alkyl groups. Examples of alkanones are acetone, 2-butanone, 3-pentanone, 3-hexanone and the like. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diasterameric salts of those instant compounds characterized by the presence of a basic amino group and an optically active acid, or by the synthesis from optically active precursors.

The present invention comprehends all optical isomers and racemic forms thereof and all geometric isomers of the compounds disclosed and claimed herein. The formulas of the compounds shown herein are intended to encompass all possible geometric and optical isomers of the compounds so depicted.

The novel 3-(1-substituted-4-piperidyl)-1,2-benzisoxazoles of formula 1, i.e., the compounds of the present invention, are prepared by the processes as herein after described.

To prepare 3-(4-piperidyl)-1,2-benzisoxazoles having a 4-fluorobenzoylalkyl group bound to the nitrogen atom of the piperidine ring, a 3-(1-substituted-4-piperidyl)-1,2-benzisoxazole of formula 2

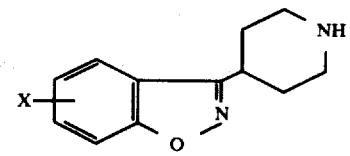

wherein X is hydrogen, halogen, alkyl, alkoxy or hydroxy, the synthesis of which is described in U.S. patent application Ser. No. 319,871, is condensed with a 4-fluorobenzoylalkyl halide ethylene glycol ketal of formula 3

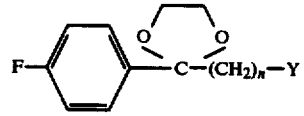

wherein Y is chloro or bromo and n is 2 or 3, to afford a 3-[1-(4-fluorobenzoylalkyl)-4-piperidyl]-1,2-benzisoxazole ethylene ketal of formula 4

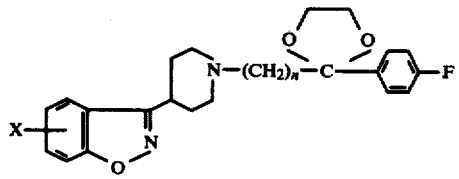

wherein X and n are as above, which is hydrolized to a 3-[1-(4-fluorobenzoylalkyl)-4-piperidyl]-1,2-benzisoxazole of formula 5

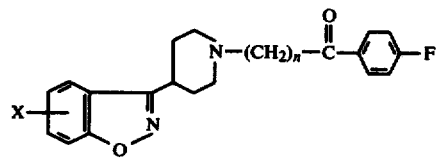

wherein X and n are as above.

The condensation is readily performed by treating the N-unsubstituted piperidine 2 with a halide 3 in the presence of an acid acceptor, a displacement promoter and a suitable solvent. Among acid acceptors, there may be mentioned alkali metal carbonates and alkali metal bicarbonates such as, for example, sodium and potassium carbonate and sodium and potassium bicarbonate. Sodium bicarbonate and potassium carbonate are preferred. Among displacement promoters, there may be mentioned alkali metal halides such as, for example, sodium and potassium iodide, and sodium and potassium bromide. Potassium iodide is preferred. Among suitable solvents, there may be mentioned polar aprotic substances such as dimethylformamide, dimethylacetamide and hexamethylphosphoramide. Dimethylformamide is preferred. The temperature at which the condensation is conducted is not narrowly critical. It is desirable, however, to perform the reaction at a temperature within the range of about 50° C. to about 130° C. to assure a reasonable rate of conversion. A reaction temperature within the range of about 80° to 110° is preferred.

The preferred 4-fluorobenzoylaklyl halide ethylene glycol ketal of formula 3 is a compound wherein Y is chloro.

The hydrolysis of the ethylene ketal moiety of a benzisoxazole of formula 4 is conveniently accomplished by conventional methods involving, for example, the interaction of a mineral acid, such as hydrochloric acid, in an alkanol, such as methanol, at ambient temperature or an elevated temperature, such as the reflux temperature of the reaction system.

Similarly, to prepare a 3-[1-(6-fluoro-1,2-benzisoxazol-3-alkyl)-4-piperidyl]-1,2-benzisoxazole, a compound of formula 1 wherein R is

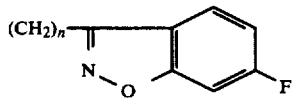

wherein n is as above, a 3-(1-unsubstituted-4-piperidyl)-1,2-benzisoxazole of formula 2 is condensed with a 3-(ω-haloalkyl)-6-fluoro-1,2-benzisoxazole of formula 6

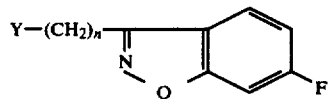

wherein Y is bromo or chloro, and n is as above, preferably a haloalkylbenzisoxazole of formula 6 wherein Y is chloro, in the presence of an alkali metal carbonate or alkali metal bicarbonate, preferably potassium carbonate or sodium bicarbonate, as an acid acceptor, and an alkali metal halide, preferably potassium iodide, as a reaction promotor in an aprotic polar solvent, preferably dimethylformamide, at a condensation temperature, preferably within the range of about 80° C. to about 100° C.

To introduce the indol-3-ylalkyl function, i.e., to fabricate a 3-{ω-[4-(1,2-benzisoxazol-3-yl)piperidyl]alkyl}indole of formula 1 wherein R is a group of the formula

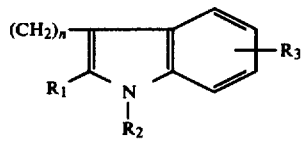

wherein R₁, R₂, R₃ and n are as above, one treats a 3-(1-unsubstituted-4-piperidyl)-1,2-benzisoxazole of formula 2, wherein X is as above with a 3-(phenylsulfonylalkyl)indole or 3-alkylphenylsulfonylalkyl)indole of formula 7

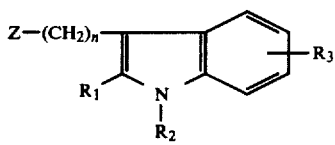

wherein Z is a group of the formula

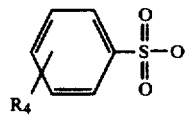

wherein R is hydrogen or alkyl and R₁, R₂, R₃ and n are as above.

The reaction involving the displacement of the phenylsulfonyl group of 7 is accomplished by treating an N-unsubstituted piperidine 2 with a sulfonyl compound 7 in an aprotic polar solvent, such as dimethylformamide, dimethylacetamide and hexamethylphosphoramide, or in an alkanone such as acetone, 2-butanone, 3-pentanone and the like, dimethylformamide and 2-butanone being preferred, in the presence of an acid scavenger such as an alkali metal carbonate (sodium or potassium carbonate) or alkali metal bicarbonate (sodium or potassium bicarbonate), potassium carbonate and sodium bicarbonate being preferred, at a temperature of about 70° to about 110°, preferably a temperature of 90° C., when an aprotic polar solvent is used, and at about the reflux temperature of the reaction system when an alkanol is employed as the solvent.

A (phenylsulfonylalkyl)indole, i.e., a compound of formula 7 wherein R₄ is hydrogen, is the preferred reaction partner.

To prepare 3-(4-piperidyl)-1,2-benzisoxazoles characterized by the presence of a 1,3-dihydro-2-oxo-2H-benzisoxazol-1-yl-alkyl group, i.e., a compound of formula 1 wherein R is

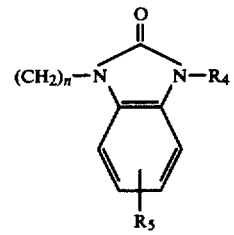

wherein R₄, R₅ and n are as above, an N-unsubstituted piperidine of formula 2 is contacted with a 1-(ω-haloalkyl)1,2-dihydro-2H-benzimidazol-2-one of formula 8

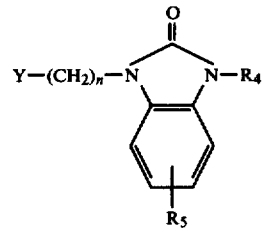

wherein Y is bromo or chloro, R₄, R₅ and n are as above in the presence of a base in an appropriate solvent. Bases include alkali metal carbonates such as, for example, sodium carbonate and potassium carbonate, and alkali metal bicarbonates such as, for example sodium bicarbonate and potassium bicarbonate. Sodium and potassium carbonates are preferred. Appropriate solvents include alkanones, for example, acetone, 2-butanone and 4-methyl-2-pentanone and the like. 4-Methyl-2-pentanone is preferred. To facilitate the displacement reaction, a promoter, for example, an alkali metal halide such as sodium or potassium iodide, is employed. While the reaction proceeds readily at moderate temperatures, it may be carried out at elevated temperatures, such as the reflux temperature of the reaction system to assure a reasonable rate of conversion.

A 1-(3-chloroalkyl-1,2-dihydro-2H-benzimidazole-2-one, i.e., a compound of 8 wherein Y is chloro, is a preferred reaction substrate.

In a like manner, to incorporate the 4,4-bis-(4-fluorophenyl)-1-butyl group into a 3-(1-unsubstituted-4-piperidyl)-1,2-benzisoxazole, i.e., to elaborate a compound of formula 9

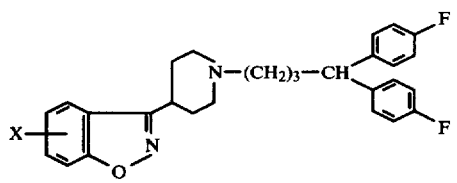

wherein X is as above, one treats a 3-(1-unsubstituted-4-piperidyl)-1,2-benzisoxazole of formula 1 wherein X is as above with a 4,4-bis-(4-fluorophenyl)butylhalide of formula 10

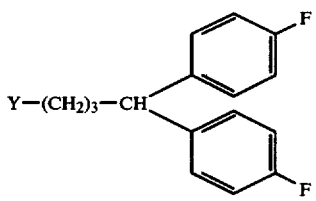

wherein Y is chloro or bromo is an aprotic polar solvent such as dimethylformamide, dimethylacetamide and hexamethylphosphoramide, in the presence of an acid acceptor such as an alkali metal carbonate, for example, sodium or potassium carbonate or an alkali metal bicarbonate, for example, sodium or potassium bicarbonate. Dimethylformamide is the preferred solvent, and potassium carbonate and sodium bicarbonate are the preferred acid acceptors. A displacement promoter such as an alkali metal halide, for example, sodium or potassium iodide may be employed to facilitate the reaction. Elevated temperatures within the range of about 50° C. to about 120° C. may also be employed to facilitate the reaction, even though the reaction temperature is not critical.

4-Fluorobenzoylalkylhalide ethylene glycol ketals of formula 3, the substrates for the preparation of 3-[1-(4-fluorobenzoyl)-alkyl]-4-piperidyl]-1,2-benzisoxazole ethylene ketals of formula 4 and 3-[1-(4-fluorobenzoylalkyl)-4-piperidyl]-1,2-benzisoxazole of formula 5, is prepared from commercially available γ-halo-4-fluoro-butyrophenones of formula 11

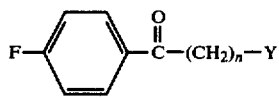

wherein Y is chloro or bromo and n is 2 or 3 by methods well known in the art. For example, treatment of -chloro-4-fluorobutyrophenone with ethylene glycol in the presence of a mineral acid such as sulfuric acid by the method described in R. B. Wagner and H. D. Zook (see "Synthetic Organic Chemistry", John Wiley and Sons, Inc., New York, N.Y., 1953, pages 262 and 263) furnishes γ-chloro-4-fluorobutyrophenone ethylene ketal.

3-(3-Haloalkyl)-6-fluoro-1,2-benzisoxazoles of formula 6, one of the starting materials for the synthesis of 3-[1-(6-fluoro-1,2-benzisoxazole-3-alkyl)-4-piperidyl]-1,2-benzisoxazoles of formula 1, is obtained by following the preparative procedures disclosed in U.S. patent application Ser. No. 257,698, filed Apr. 27, 1981.

3-(Phenylsulfonylalkyl)indoles and 3-(alkylphenylsulfonylalkyl)indoles of formula 7, precursors for the preparation of 3-{3-[4-(1,2-benzisoxazol-3-yl)piperidyl]alkyl}indoles of formula 1, are constructed by conventional processes, involving the interaction of a hydrazine of formula 12 wherein $R_2$ is hydrogen or alkyl and $R_3$ is hydrogen, halogen or alkyl, with a ketoacid or aldehydoacid of formula 13, wherein $R_1$ is hydrogen or alkyl and n is 2 or 3 under the condition of the Fischer indole sysnthesis (R. B. Wagner and H. D. Zook, ibid., page 844) to form an indol-3-yl-alkanoic acid ester of formula 15 wherein $R_1$, $R_2$, $R_3$ and n are as above and $R_6$ is alkyl, followed by reduction of the ester group of the compound of formula 15 with lithium aluminum hydride to afford an indol-3yl-alkanol of formula 16 wherein $R_1$, $R_2$, $R_3$ and n are as above (R. B. Wagner and H. D. Zook, ibid., page 155), which, in turn, is converted to the sulfonyl derivative 18 by means of a sulfonylhalide of formula 17, wherein $R^7$ is phenyl or alkylphenyl and V is chloro or bromo (R. B. Wagner and H. D. Zook, ibid., page 823). See Scheme A).

1-(3-Haloalkyl)-1,2-dihydro-2H-benzimidazol-2-one of formula 8 reactants for the synthesis of 3-{1-[1,3-dihydro-2-oxo-2H-benzimidazol-1-ylalkyl]-4-piperidyl}-1,2-benzisoxazoles of formula 1 are prepared by the processes described by J. Davall and D. H. Lang in J. Chem. Socl, 314 (1960) and by J. Vandenmark, et al., in U.S. Pat. No. 4,066,772, granted Jan. 3, 1976.

Precursors for the elaboration of 3-{1-[4,4-bis(4-fluorophenyl)-1-alkyl]-4-piperidyl}-1,2-benzisoxazoles of formula 1, namely, halo-1,1-bis(4-fluorophenyl)alkanes of formula 10, are prepared according to the procedure disclosed by P. A. J. Janssen in U.S. Pat. No. 3,238,216, granted Mar. 1, 1966; Chem Abs., 65, 8922f (1966). For example, as depicted below, ethyl cyclopropyl carboxylate 19 is treated with the Grignard reagent of 4-fluorobromo benzene 20 to afford the carbinol 21 which is treated with a thionylhalide to furnish a butenyl halide 22. Catalytic hydrogenation of butenyl halide 22 yields 4,4-bis(4-fluorophenyl)butyl halide 23. (See Scheme B).

The 3-(1-unsubstituted-4-piperidyl)-1,2-benzisoxazoles of the present invention are useful for treating psychoses by virtue of their ability to elicit a neuroleptic response in mammals.

Neuroleptic activity is determined in the climbing mice assay by a method similar to those described by P. Protais, et al., Psychopharmacol., 50, 1 (1976) and B. Costall, Eur. J. Pharmacol., 50, 39 (1978).

The subject CK-1 male mice (23-27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be test for neuroleptic activity are injected intraperitoneally 30 minutes prior to the apomorphine challenge at a screening does of 10 mg/kg.

For evaluation of climbing, 3 readings are taken at 10, 20 and 30 minutes after apomorphine administration according to the following scale:

| Climbing Behavior | Score |
|---|---|
| Mice with: | |
| 4 paws on bottom (no climbing) | 0 |
| 2 paws on the wall (rearing) | 1 |
| 4 paws on the wall (full climb) | 2 |

Mice consistently climbing before the injection of apormorphine will be discarded.

With full-developed apomorphine climbing, the animals are hanging onto the cage walls, rather motionless, over longer periods of time. By contrast, climbs due to mere motor stimulation usually only last a few seconds.

The climbing scores are individually totaled (maximal score: 6 per mouse over 3 readings) and the total score of the control group (vehicle intraperitoneally—apomorphine subcutaneously) is set to 100%. $ED_{50}$ values with 95% confidence limits, calculated by a Linear Regression Analysis of some of the instant 4-piperidyl)-1,2-benzisoxazoles as well as standard neuroleptics, are presented in the Table.

TABLE

| COMPOUND | NEUROLEPTIC ACTIVITY ($ED_{50}$ mg/kg) |
|---|---|
| 3-[1-(4-fluorobenzoyl)propyl-4-piperidyl]-6-chloro-1,2-benzisoxazole hydrochloride | 0.27 |
| 6-fluoro-3-{1-[4,4-bis(4-fluorophenyl)-1-butyl]-4-piperidyl}-1,2-benzisoxazole hydrobromide | 0.58 |
| 3-{1-[1,3-dihydro-2-oxo-2H-benzimidazole-1-ylethyl]-4-piperidyl}-1,2-benzisoxazole hydrobromide | 7.7 |
| 3-[1-(6-fluoro-1,2-benzisoxazol-3-propyl)-4-piperidyl]-5-fluoro-1,2-benzisoxazole hydrochloride | 3.4 |
| 3-{3-[4-(6-fluoro-1,2-benzisoxazol-3-yl)-piperidyl]propyl}-2-methylindole hydrochloride | 0.16 |
| 3-{1-[1,3-dihdro-2-oxo-2H-benzimidazol-1-yl-propyl]-4-piperidyl}-1,2-benzisoxazole | 0.36 |
| 3-[1-(6-fluoro-1,2-benzisoxazol-3-propyl)-4-piperidyl]-5-methoxy-1,2-benzisoxazole hydrobromide | 7.23 |
| 6-chloro-3-{1-[4,4-bis(4-fluorophenyl)-1-butyl]-4-piperidyl}-1,2-benzisoxazole hydrochloride | 6.4 |
| 3-{1-[4,4-bis-(4-fluorophenyl)-1-butyl]-4-piperidyl}-5-fluoro-1,2-benzisoxazole hydrochloride | 1.6 |
| haloperidol (standard) | 0.11 |
| sulpiride (standard) | 14.5 |

Compounds of the invention also include:
(a) 3-[1-(4-fluorobenzoylpropyl)-4-piperidyl]-1,2-benzisoxazole;
(b) 3-[1(6-fluoro-1,2-benzisoxazol-3-propyl)-4-piperidyl]-1,2-benzisoxazole;
(c) 3-{3-[4-(1,2-benzisoxazol-3-yl)-piperidyl]ethyl}-2-methylindole;
(d) 3-{3-[4-(1,2-benzisoxazol-3-yl)piperidyl]propyl}indole;
(e) 3-{3-[4-(1,2-benzisoxazol-3-yl)piperidyl]propyl}-1-methylindole;
(f) 3-{3-[4-(1,2-benzisoxazol-3-yl)-piperidyl]propyl}-5-methylindole;
(g) 3-{3-[4-(1,2-benzisoxazol-3-yl)-piperidyl]propyl}-6-chloroindole;
(h) 3-{1-[1,3-dihydro-3-methyl-2-oxo-2H-benzimidazol-1-ylpropyl]-4-piperidyl}-1,2-benzisoxazole;
(i) 3-{1-[1,3-dihydro-6-chloro-2-oxo-2H-benzimidazol-1-ylpropyl]-4-piperidyl}-1,2-benzisoxazole;
(j) 3-{1-[1,3-dihydro-5-methyl-2-oxo-2H-benzimidazol-1-ylpropyl]-4-piperidyl}-1,2-benzisoxazole; and
(k) 3-[1-(4-fluorobenzoylpropyl)-4-piperidyl]-5-methyl-1,2-benzisoxazole.

Antipsychotic response is achieved when the present 3-(1-substituted-4-piperidyl)-1,2-benzisoxazoles are administered to a subject requiring such treatment as an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preprations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, Primogel, corn starch and the like; a lubricant such as magnesium stearate or Sterotes; a glidant such as colloida silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

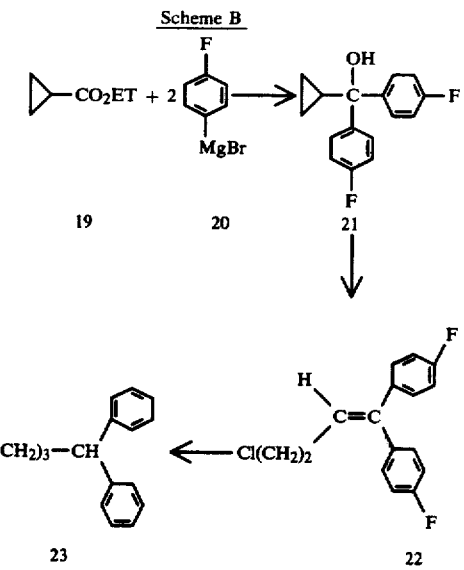

The following Examples are for illustrative purposes only and are not to be construed as limiting the invention. Temperatures are in degrees Centigrade (°C.). Half-saturated sodium chloride solution is prepared by adding an equal volume of water to saturated sodium chloride solution.

EXAMPLE 1

3-[1-(4-Fluorbenzoylpropyl)-4-piperidyl]-1,2-benzisoxazole hydrochloride

A suspension of 4.3 g of 4-piperidyl-1,2-benzisoxazole, 5.5 g of sodium bicarbonate, 3.0 g of potassium iodide and 5.7 g of γ-chloro-4-fluoro-butyrophenone ethylene glycol ketal in 90 ml of dimethylformamide was stirred for 20 hrs at 80°. The reaction mixture was

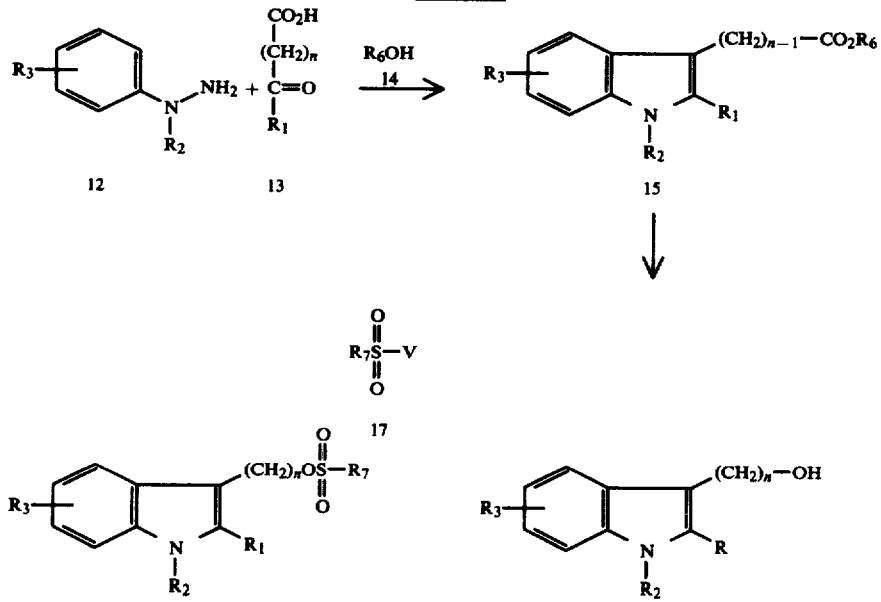

wherein $R_1$ and $R_2$ are each independently hydrogen or alkyl, $R_3$ is hydrogen, halogen or alkyl, and n is 2 or 3.

cooled to room temperature, filtered, poured into 1 l of water and extracted with ether (3 times). The ether was removed under reduced pressure and the residue was stirred at room temperature for 15 mins in 100 ml of methanol and 50 ml of 3 N hydrochloric acid. The reaction mixture was filtered. The solid was dissolved in ether into which hydrochloric acid was bubbled. The precipitate was filtered and recrystallized twice from ethanol to give 3.0 g (37%) of product, mp 231°–233°.

ANALYSIS: Calculated for $C_{22}H_{23}FN_2O_2$ HCl: 65.85%C, 6.00%H, 6.96%N; Found: 65.77%C, 5.99%H, 7.00%N.

EXAMPLE 2

3-[1-(4-Fluorobenzoylpropyl)-4-piperidyl]-6-fluoro-1,2-benzisoxazole hydrochloride a. A mixture of 3.95 g of 3-(4-piperidyl)-6-fluoro-1,2-benzisoxazole, 5 g of sodium bicarbonate, 2.7 g of potassium iodide and 5.2 g of γ-chloro-4-fluorobutyrophenone ethylene glycol ketal in 81 ml of dimethylformamide was stirred for 20 hrs at 80°–90°, filtered and poured into a mixture of 1.2 l of water, 300 ml of saturated sodium chloride solution and 40 ml of ethanol. The oil was collected, dissolved in 50 ml of dichloromethane and the solution was washed with 100 ml of potassium carbonate solution and 200 ml of water. Evaporation gave 7.8 g of 3-[1-(4-fluorobenzoylpropyl)-4-piperidyl]-6-fluoro-1,2-benzisoxazole ethylene ketal as an oil.

b. A mixture of 7.8 g of the ketal in 300 ml of methanol and 150 ml of hydrochloric acid was stirred at room temperature for 15 mins and under reflux for 15 mins. After 20 mins, about 300 ml of methanol-water was distilled. Hot water (80°, 2.5 l) was added in equal portions and decanted three times. The suspension was filtered and extracted 3 times with about 1600 ml of ether. The aqueous phase was made alkaline with sodium hydroxide solution extracted three times with 2 l of dichloromethane to yield, after evaporation of the solvents, a residue. Recrystallization from isopropanol gave 2.1 g (31.3%) of product, mp 101°–103°, as the free base.

c. A 3.1 g sample of the base was dissolved in 80 ml of methanol and 1.5 ml of concentrated hydrochloric acid was added. After 5 mins, the solution was evaporated in vacuum and 80 ml of benzene was added. After evaporation of the benzene, the residue was triturated with 100 ml of ether and recrystallized from 100 ml of methanol/40 ml of isopropanol to give 2.53 g of the hydrochloride, mp 224°–225°. An additional 0.42 g was obtained from the mother liquors. Total yield of 2.95 g (39.2%).

ANALYSIS: Calculated for $C_{22}H_{22}F_2N_2O_2$ HCL: 62.80%C, 5.27%H, 6.65%N, 8.42%Cl; Found: 62.35%C, 5.50%N, 6.56%N, 8.21%Cl.

EXAMPLE 3

3-[1-(4-Fluorobenzoylpropyl)-4-piperidyl]-6-chloro-1,2-benzisoxazole hydrochloride A mixture of 4.26 g of 3-(4-piperidyl)-6-chloro-1,2-benzisoxazole, 2.3 g of anhydrous potassium carbonate and 6.3 g of γ-chloro-4-fluorobutyrophenone ethylene ketal in 45 ml of dimethylformamide was stirred for 5.5 hrs at 100°–110°, cooled to 20°, and 35 ml of dimethylformamide was distilled in vacuo. The residue was added to 800 ml of half saturated sodium chloride solution and 40 ml of ethanol. The oil was collected, triturated three times with 600 ml water and dissolved in 300 ml of dichloromethane. The solution was washed with 350 ml half-saturated sodium chloride solution and water and extracted with 200 ml of dichloromethane. The combined dichloromethane from all extracts were distilled to yield 9.7 g of 3-[1-(4-fluorobenzoylpropyl)-4-piperidyl]-6-chloro-1,2-benzisoxazole ethylene ketal. A 9.7 g sample of the ketal in 80 ml of methanol, 15 ml of water and 7.5 ml of concentrated hydrochloric acid was heated under reflux for 1 hr. The methanol and water were distilled. Benzene (80 ml) was added and distilled. The residue was triturated twice with 100 ml ether. The residue was dissolved in 200 ml of isopropanol and 150 ml of methanol. The solvents were slowly distilled to a final volume of ca 100 ml, whereby the hydrochloride salt precipitates. After 18 hrs, the solid was collected, washed with isopropanol and dried. Recrystallization twice from 50 ml of isopropanol/20 ml of methanol and 30 ml of isopropanol/20 ml of ethanol/100 ml of ether yielded 4.5 g (57.2%) of product, mp 234°–235°.

ANALYSIS: Calculated for $C_{22}H_{23}FCl_2N_2O_2$: 60.41%C, 5.30%H, 6.45%N; Found: 60.65%C, 5.41%H, 6.29%N.

EXAMPLE 4

3-{1-[4,4-bis(4-Fluorophenyl)-1-butyl]-4-piperidyl}-1,2-benzisoxazole hydrochloride A mixture of 3.94 g of 3-(4-piperidyl)-1,2-benzisoxazole hydrochloride, 4.60 g of 4-chloro-1,1-bis(4-fluorophenyl)butane, 4.95 g of anhydrous potassium carbonate, a few crystals of potassium iodide and 85 ml of dimethylformamide were stirred and heated at 90° for 8 hrs and then stirred at ambient temperature over the weekend. The mixture was poured into water and extracted with ethyl acetate and saturated sodium chloride solution, dried over anhydrous magnesium sulfate and the solvent was removed in vacuo to yield an oil. The oil was dissolved in anhydrous diethyl ether and a sautrated hydrogen chloride-ether solution was added dropwise to precipitate a gum. The gum was recrystallized from ethyl acetate-ether to yield a solid. The mother liquor was concentrated to yield an additional solid. The solids were combined and recrystallized twice from ethyl acetate-ether to yield 2.35 g (29.5%) of product, mp, 156°–157°.

ANALYSIS: Calculated for $C_{28}H_{28}F_2N_2O$ HCl: 69.63%C, 6.05%H, 5.80%N; Found: 69.65%C, 6.10%H, 5.94%N.

EXAMPLE 5

6-Fluoro-3-{1-[4,4-bis(4-fluorophenyl)-1-butyl]-4-piperidyl}-1,2-benzisoxable hydrobromide A mixture of 3.9 g of 6-fluoro-3-(4-piperidyl)-1,2-benzisoxazole hydrochloride, 5.5 g of 4-chloro-1,1-bis(4-fluorophenyl)butane, 5.5 g of anhydrous potassium carbonate and 45 ml of dimethylformamide was stirred and heated at 100° for 8 hrs. The reaction mixture was poured into water; the aqueous mixture was extracted with ether. The ether extract was washed with water, dried over anhydrous magnesium sulfate and the ether was removed under reduced pressure to yield an oil. The oil was dissolved in ether and hydrogen chloride was added to precipitate a gum, which upon triturating with ethyl acetate yielded a solid. The salt was converted to its free base (sodium hydroxide solution) and chromatographed on a 100 g of silica gel using chloroform as the eluent. The resulting oil was dissolved in absolute ether and a saturated ethanol-hydrogen bromide solution was added until precipitation was complete. The product was recrystallized from ethanol-ether to give 2.2 g (26.8%) of product, mp 202°–204°.

ANALYSIS: Calculated for $C_{28}H_{27}F_3N_2O$ HBr: 61.65%C, 5.17%H, 5.14%N; Found: 61.61%C, 5.23%H, 4.99%N.

EXAMPLE 6

3-{1-[4,4-bis-Fluorophenyl)-1-butyl]-4-piperidyl}-5-fluoro-1,2-benzisoxazole hydrochloride A mixture of 3.3 g of 5-fluoro-3-(4-piperidyl)-1,2-benzisoxazole hydrochloride, 3.9 g of 4-chloro-1,1-bis-(4-fluorophenyl)butane 3.9 g of anhydrous potassium carbonate, a few crystals of potassium iodide and 65 ml of dimethylformamide was stirred under nitrogen at 90° for 8 hrs. The reaction mixture was poured into water and the aqueous suspension was extracted with ethyl acetate. The extract was washed with water, brine and then was dried over anhydrous magnesium sulfate. Evaporation of the solvent gave an oil, which was converted to a hydrochloride salt with ether-hydrogen chloride. The salt was recrystallized twice from ethanol-ether and then from ethanol to yield 2.1 g (32.3%) of product, mp, 190°–192°.

ANALYSIS: Calculated for $C_{27}H_{27}F_3N_2O$ HCl: 67.12%C, 5.63%H, 5.59%N; Found: 66.45%C, 5.62%H, 5.97%N.

EXAMPLE 7

3-{1-[4,4-bis(4-Fluorophenyl)-1-butyl]-4-piperidyl}-5-methoxy-1,2-benzisoxazole hydrobromide A mixture of 3.5 g of 5-methoxy-3-(4-piperidyl)-1,2-benzisoxazole hydrochloride, 3.9 g of 4-chloro-1,1-bis(4-fluorophenyl)butane, 3.9 g of anhydrous potassium carbonate, a few crystals of potassium iodide and 65 ml of dimethylformamide was stirred and heated at 90° for 8 hrs. The reaction mixture was poured into water and the aqueous mixture was extracted with ethyl acetate. The ethyl acetate extract was washed with water and saturated sodium chloride solution, dried over anhydrous magnesium sulfate and the solvent was removed under reduced pressure to yield an oil. The oil was filtered through a silica gel column (90 g), using acetone as eluent. The oil was dissolved in anhydrous ether and a saturated hydrogen bromide-ether solution was added to precipitate the salt. The salt was recrystallized twice from methanol-ether to yield 2.8 g (38.8%) of product, mp, 214°–216°.

ANALYSIS: Calculated for $C_{29}H_{30}F_2N_2O_2$ HBr: 62.48%C, 5.61%H, 5.03%N; Found: 62.47%C, 5.67%H, 5.03%N.

EXAMPLE 8

3-{1-[4,4-bis(4-Fluorophenyl)-1-butyl]-4-piperidyl}-5-hydroxy-1,2-benzisoxazole hydrochloride A mixture of 1.5 g of 5-hydroxy-3-(4-piperidyl)-1,2-benzisoxazole hydrobromide, 0.84 g of sodium bicarbonate, 25 ml of dimethylformamide, a few crystals of potassium iodide and 1.4 g of 4-chloro-1,1-bis(4-fluorophenyl)butane was stirred at 90° for 8 hrs. After cooling to ambient temperature, the mixture was poured into water and the aqueous mixture was extracted with ethyl acetate. The ethyl acetate was washed with water and brine, and the the solvent was removed in vacuo to yield a solid. The solid was triturated with ether and was filtered. The filter cake was partially dissolved in ethanol and a saturated methanol-hydrogen chloride solution was added, followed by warming to obtain a solution. The salt was precipitated by adding ether. Two recrystallizations from ethanol-ether afforded 1.0 g (40%) of product, mp 234°–236°.

ANALYSIS: Calculated for $C_{28}H_{28}F_2N_2O_2$ HCl: 67.39%C, 5.86%H, 5.62%N; Found: 67.24%C, 5.86%H, 5.44%N.

EXAMPLE 9

6-Chloro-3{1-[4,4-bis(4-fluorophenyl)-1-butyl]-4-piperidyl}-1,2-benzisoxazole hydrochloride A mixture of 16.5 g of 6-chloro-3-(4-piperidyl)-1,2-benzisoxazole, 22.4 g of 4-chloro-1,1-bis(4-fluorophenyl)butane, 22.0 g of potassium carbonate and 200 ml of dimethylformamide was stirred and heated at 75° for 5 hrs. The reaction mixture was allowed to cool and was filtered. The filtrate was concentrated in vacuo to an oil, which was taken up in 300 ml ether and washed with an equal portion of brine. The ether layer was dried over anhydrous sodium sulfate and concentrated in vacuo to an oil. The oil was dissolved in 65 ml of ethanol, the solution was cooled, and 20 ml of ether saturated with hydrogen chloride was added dropwise. Ether (400 ml) was added causing turbidity. The mixture was seeded and then stirred for ½ hour to produce the salt. Recrystallization from 800 l of 3:5 ethanol-ether gave 11.3 g (13% yield) of product, mp 205°–207°.

ANALYSIS: Calculated for $C_{28}H_{27}ClF_2N_2O$ HCl: 64.99%C, 5.45%H, 5.41%N; Found: 64.75%C, 5.43%H, 5.51%N.

EXAMPLE 10

5,6-Dimethoxy-3-{1-[4,4-bis(4-fluorophenyl)-1-butyl]-4-piperidyl}-1,2-benzisoxazole hydrobromide A stirred mixture of 2.60 g of 5,6-dimethoxy-3-(4-piperidyl)-1,2-benzisoxazole hydrobromide, 3.30 g of potassium carbonate, 0.25 g of potassium iodide, 2.20 g of 4-chloro-1,1-bis(4-fluorophenyl)butane and 75 ml of dimethylformamide was heated to 90° for 8 hrs and overnight at ambient temperature. The reaction mixture was poured into 500 ml of water and was extracted with ether, dried over anhydrous magnesium sulfate and the solvent was removed in vacuo to yield an oil. The oil was purified by filtering through a silica gel column (25:1), using dichloromethane as eluent. The eluent was evaporated and the residue was dissolved in ether, and a saturated hydrogen bromide-ether solution was added dropwise to precipitate the salt. The salt was collected and washed with 3.0 g of ether. Recrystallization from toluene-water yielded 2.2 g (48.3%) of the product, mp 195°–197°.

ANALYSIS: Calculated for $C_{30}H_{32}F_2N_2O_3$ HBr: 61.34%C, 5.45%H, 4.77%N; Found: 61.18%C, 5.66%H, 4.65%N.

EXAMPLE 11

3-{3-[4-(1,2-benzisoxazol-3-yl)piperidyl]propyl}-2-methylindole

A mixture of 1.67 g of 3-(4-piperidyl)-1,2-benzisoxazole hydrochloride, 2.47 g of 2-methyl-3-(phenylsulfonylpropyl)indole, 40 ml of dimethylformamide and 5.0 g of potassium carbonate was stirred under nitrogen at 90° for 4 hrs. The reaction mixture was poured into water. The precipitate was extracted with ethyl acetate and the ethyl acetate was washed with brine, dried over anhydrous magnesium sulfate and the solvent was removed in vacuo to yield an oil. The oil was combined with 1.39 g of previously prepared material and the sample was chromatographed in 120 g of silica gel, using 1% methanol-chloroform as eluent. The eluent was evaporated and the residue was recrystallized two times from ethanol-water to yield 1.60 g (15.4%) of the product, mp 110°-112°.

ANALYSIS: Calculated for $C_{24}H_{27}N_3O$: 77.18%C, 7.23%H, 11.25%N; Found: 76.86%C, 7.29%H, 11.09%N.

EXAMPLE 12

3-{3-[4-(6-Fluoro-1,2-benzisoxazol-3-yl)piperidyl]-propyl}-2-methylindole

A stirred mixture of 3.1 g of 2-methyl-3-(3-phenylsulfonylpropylindole, 2.1 g of 6-fluoro-3-(4-piperidyl)-1,2-benzisoxazole hydrochloride, 6.3 g of potassium carbonate and 50 ml of 2-butanone was heated under reflux for 24 hrs. The reaction mixture was poured into water and the aqueous mixture was extracted with dichloromethane. The organic extract was washed with water, dried over anhydrous magnesium sulfate and the solvent was removed under reduced pressure. The resultant oil was triturated with isopropyl ether and the solid was collected. The solid was combined with a 1.6 g sample of previously prepared material and the combined sample was chromatographed on 100 g silica gel, using 2% methanol-chloroform as eluent. The eluent was evaporated and the solid was dissolved in 125 ml toluene and a saturated hydrogen chloride-toluene solution was added until no more precipitate formed. The precipitate was filtered and dried. Recrystallization from acetone afforded 2.7 g (31.5%) of product, mp 208°-210°.

ANALYSIS: Calculated for $C_{24}H_{26}FN_3O$ HCl: 67.36%C, 6.36%H, 9.82%N; Found: 67.30%C, 6.40%H, 9.60%N.

EXAMPLE 13

3-{3-[4-(6-Chloro-1,2-benzisoxazol-3-yl)piperidyl]-propyl}2-methylindole

A stirred mixture, under nitrogen, of 27.0 g of 3-(4-piperidyl-6-chloro-1,2-benzisoxazole, 31.3 g of 2-methyl-3-(3-phenylsulfonylpropyl)indole and 27.6 g of anhydrous potassium carbonate in 500 ml of methyl ethyl ketone was heated under reflux for 6 hrs. The mixture was cooled and treated with 150 ml of water. The organic phase was separated, extracted with water and concentrated to an oily residue. The residue was dissolved in 50 ml of ethyl acetate and absorbed on a chromatography column containing 300 g of silica gel packed in ethyl acetate. Elution with ethyl acetate, followed by concentration of the eluent and trituration with ether, provided 12.1 g (31% yield) of product. Recrystallization from a small volume of toluene afforded the anlytical sample, mp 108°-110°.

ANALYSIS: Calculated for $C_{24}H_{26}ClN_3O$: 70.66%C, 6.42%, 10.30%N; Found: 70.76%C, 6.43%H, 10.25%N.

EXAMPLE 14

3-{3-[4-(5-Methoxy-1,2-benzisoxazole-3-yl)piperidyl]-propyl-2-methylindole hydrochloride A mixture of 4.0 g of 2-methyl-3-(3-phenylsulfonylpropyl)indole, 3.0 g of 5-methoxy-3-(4-piperidyl)-1,2-benzisoxazole hydrochloride, 8.0 g of potassium carbonate and 70 ml of 2-butanone was heated under reflux, with stirring, and refluxed under nitrogen for 16 hours. The reaction mixture was poured into water and the aqueous suspension was extracted with ethyl acetate. The insoluble material was collected and washed with diluted sodium hydroxide to give a solid. The ethylacetate extract was washed with water, dried over anhydrous magnesium sulfate and the solvent was removed in vacuo to give an additional solid. Treatment of the combined solids with a saturated hydrogen chloride-toluene solution gave the salt. The salt was triturated with acetone and recrystallized from ethanol-ether to give an ethanolate, mp 163°-165° (foaming). Recrystallization of the alcoholate from acetonitrile and subsequent drying of the sample at 100° and ca 1 mm gave 1.60 g (33%) of product, mp 130°-132°.

ANALYSIS: Calculated for $C_{25}H_{29}N_3O_2$ HCl: 68.24%C, 6.87%H, 9.55%N; Found: 68.16%C, 7.01%H, 9.31%N.

EXAMPLE 15

3-{3-]4-(5-Hydroxy-1,2-benzisoxazol-3-yl)piperidyl]-propyl-2-methylindole hydrochloride A mixture of 3.4 g of 5-hydroxy-3-(4-piperidyl)-1,2-benzisoxazole hydrochloride, 2.5 g of sodium bicarbonate and 4.1 g (0.013 mole) of 2-methyl-3-(phenylsulfonylpropyl)indole and 50 ml of dimethylformamide was stirred under nitrogen at 90° for 4 hrs. The reaction mixture was poured into water and the solid was collected. The solid was triturated with ethyl acetate and ethereal hydrogen chloride was added to the ethyl acetate to precipitate the hydrochloride salt. The salt was recrystallized from ethanol-ether and triturated with ethyl acetate to give 1.6 g (34.0%) of product, mp 230°-232°.

ANALYSIS: Calculated for $C_{24}H_{27}N_3O_2$ HCl: 67.67%C, 6.63%H, 9.87%N; Found: 67.29%C, 6.57%H, 9.74%N.

EXAMPLE 16

3-{1,3-dihydro-2-oxo-2H-benzmidazol-1-ylpropyl]-4-piperidyl}-1,2-benzisoxazole

To a stirred mixture, under an atmosphere of nitrogen, was added 5.0 g of 3-(4-piperidyl)-1,2-benzisoxazole, 300 ml of methyl isobutyl ketone, 0.41 g of potassium iodide, 5.25 g of sodium bicarbonate and 4.93 g of 1-(3-chloropropyl)-1,2-dihydro-2H-benzimidazol-2-one. The mixture was heated under reflux for 6 hrs and stirred overnight at ambient temperature. The mixture was poured into water, extracted with dichloromethane, dried over anhydrous magnesium sulfate and the solvent was removed in vacuo to yield a solid. The solid was converted to the hydrobromide salt and the free base was regenerated. Recrystallized of a 3.10 g sample two times from ethylacetate yielded 2.10 g (22.6%) of product, mp 184°-186°.

ANALYSIS: Calculated for $C_{22}H_{24}N_4O_2$: 70.19%C, 6.43%H, 14.88%N; Found: 70.27%C, 6.44%H, 14.81%N.

EXAMPLE 17

3-{1-[1,3-Dihydro-2-oxo-2H-benzimidazol-1-ylethyl]-4-piperidyl}1,2-benzisoxazole hydrobromide To a stirred mixture, under a nitrogen atmosphere, was added 5.0 g of 3-(4-piperidyl)-1,2-benzisoxazole, 4.06 g of 1-(3-chloroethyl)-1,3-dihydro-2H-benzimidazole-2-one, 5.25 g, of anhydrous potassium carbonate, a few crystals of potassium iodide and 300 ml of 4-methyl-2-pentanone. The reaction mixture was poured into 500 ml of water and extracted with dichloromethane. The dichloromethane layer was washed with brine and the solvent was removed in vacuo to yield an oil. The oil was dissolved in ethanol and ether-hydrogen bromide solution was added dropwise to yield a solid. Recrystallization from ethanol-ether and from methanol afforded 2.20 g (20.1%) of product, mp 244°–245°.

ANALYSIS: Calculated for $C_{21}H_{22}N_4O_2$ HBr: 56.89%C, 5.23%H, 12.64%N; Found: 56.62%C, 5.10%H, 12.49%N.

EXAMPLE 18

6-Chloro-3-{1-[1,3-dihydro-2-oxo-2H-benzimidazol-1-ylpropyl]-4-piperidyl}-1,2-benzisoxazole hydrobromide A stirred mixture, under nitrogen, of 18.9 g of 3-(4-piperidyl)-6-chloro-1,2-benzisoxazole, 16.9 g of 1-(3-chloropropyl)-1,3-dihydro-2H-benzimidazol-2-one, 17.0 g of anhydrous sodium carbonate and 1.33 g of pulverized potassium iodide in 1000 ml of 2-methyl-4-pentanone was heated under reflux for 6 hrs. The solvent was removed and the residue was partitioned between 500 ml of dichloromethane and 250 ml of water. The organic phase was separated, washed three times with brine, dried under anhydrous sodium sulfate and concentrated, first at aspirator pressure in a 100° bath, then with the high-vacuum pump attached to yield an oil. The oil was dissolved in 150 ml of ethanol. The solution was cooled and stirred, while 50 ml of ethanol, freshly saturated with gaseous hydrogen bromide, was added over a 5-min period. After stirring 1 hr more in the cold, the salt was collected, filtered, washed twice with ethanol and dried to afford 16.0 g (53%) of product, mp 231°–237° dec.

ANALYSIS: Calculated for $C_{22}H_{23}ClN_4O_2$ HBr: 53.73%C, 4.92%H, 11.39%N; Found: 53.47%C, 4.94%H, 11.16%N.

EXAMPLE 19

6-Chloro-3-{1-[1,3-dihydro-2-oxo-2H-benzimidazol-1-ylethyl]-4-piperidyl}-1,2-benzisoxazole hydrochloride A stirred mixture, under nitrogen, of 10.7 g of 3-(4-piperidyl)-6-chloro-1,2-benzisoxazole, 8.3 g of 1-(2-chloroethyl)-1,3-dihydro-2H-benzimidazol-2-one, 9.54 g of anhydrous sodium carbonate and 0.75 g of pulverized potassium iodide in 500 ml of 2-methyl-4-pentanone was heated under reflux for 6 hrs. and the solvent was then removed. The residue was partitioned between 300 ml of dichloromethane and 300 ml of water. The organic phase was separated, washed three times with brine, dried over anhydrous sodium sulfate and concentrated, first at aspirator pressure in a 100° bath, then with a high vacuum pump attached, to give an oil. The oil was dissolved in 70 ml ethanol, with warming. The solution was cooled and stirred while 50 ml of saturated ethereal hydrogen chloride was added over a 10-min period. A additional 150 ml of ether was added. The salt was collected, washed twice with 1:4 ethanol-ether, twice with ether, twice with hexane and dried to afford 8.1 g (42%) of product, mp 252°–254°. The analytical sample prepared by recrystallization from methanol had mp 253°–255°.

ANALYSIS: Calculated for $C_{21}H_{21}ClN_4O_2$ HCl: 58.21%C, 5.12%H, 12.93%N; Found: 58.06%C, 5.20%H, 12.97%N.

EXAMPLE 20

5-Fluoro-3-{1-[1,3-dihydro-2-oxo-2H-benzimidazol-1-ylpropyl]-4-piperidyl}-1,2-benzisoxazole A mixture of 3.9 g of 5-fluoro-3-(4-piperidyl)-1,2-benzisoxazole, 3.8 g of 1-(3-chloropropyl)-1,3-dihydro-2H-benzimidazol-2-one, 2.7 g of sodium carbonate, a few crystals of potassium iodide and 140 ml of 2-methyl-4-pentanone was stirred and was heated under reflux under nitrogen for 8 hrs. After stirring at ambient temperature for 12 hrs, the mixture was filtered and the filter cake was stirred with 200 ml of water. The solid was collected and dried. Recrystallization from methanol-dimethylformamide-water gave 2.5 g (35.8%) of product. The product was combined with 1.0 g of that from another run to yield a total of 3.5 g of product, mp 202°–204°.

ANALYSIS: Calculated for $C_{22}H_{23}FN_4O_2$: 66.99%C, 5.88%H, 14.21%N; Found: 66.91%C, 6.03%H, 14.10%N.

EXAMPLE 21

6-Fluoro-3-{1-[1,3-dihydro-2-oxo-2H-benzimidazol-1-ylpropyl]-4-piperidyl}-1,2-benzisoxazole A mixture of 5.0 g of 6-fluoro-3-(4-piperidyl)-1,2-benzisoxazole, 4.8 g of sodium carbonate, a few crystals of potassium iodide and 175 ml of 2-methyl-4-pentanone was heated under reflux for 12 hrs. The mixture was poured into water and the organic phase was separated. The aqueous mixture was extracted with dichloromethane and added to the previously separated organic phase. The organic extract was washed with water, dried over anhydrous magnesium sulfate and the solvent was removed in vacuo to yield a solid. Chromatography of the solid on a Waters Prep 500 (two silica gel columns) and eluting with 5% methanol-dichloromethane provided a solid. Recrystallization from ethanol-water and then from ethanol (charcoal) yielded 2.4 g of product, mp 175°–177°.

ANALYSIS: Calculated for $C_{22}H_{23}FN_4O_2$: 66.99%C, 5.88%H, 14.21%N; Found: 66.95%C, 5.94%H, 13.88%N.

EXAMPLE 22

6-Methoxy-3-{1-[1,3-dihydro-2-oxo-2H-benzimidazol-1-ylpropyl]-4-piperidyl}-1,2-benzisoxazole A mixture of 4.1 g of 6-methoxy-3-(4-piperidyl)-1,2-benzisoxazole, 3.7 g of 1-(3-chloropropyl)-1,3-dihydro-2H-benzimidazol-2-one, 3.1 g of sodium carbonate, a few crystals of potassium iodide and 125 ml of 2-methyl-4-pentanone was stirred and heated under reflux under nitrogen for 16 hrs. The reaction was poured into 300 ml of water, the layers were separated and the aqueous layer was extracted twice with dichloromethane. The organic layers were combined, washed with water, dried over anhydrous magnesium sulfate and the solvent removed in vacuo to yield an oil. The oil was triturated with ether and the solid was collected. The solid was recrystallized twice from toluene to yield 2.7 g (37.7%) of product, mp 176°–178°.

ANALYSIS: Calculated for $C_{23}H_{26}N_4O_3$: 67.96%C, 6.44%H, 13.78%N; Found: 68.32%C, 6.48%H, 13.57%N.

EXAMPLE 23

3-[1-(6-Fluoro-1,2-benzisoxazole-3-propyl)-4-piperidyl]-1,2-benzisoxazole hydrobromide A mixture of 1.55 g of 3-(4-piperidyl-1,2-benzisoxazole hydrochloride, 2.00 g of 3-(3-chloropropyl)-6-fluoro-1,2-benzisoxazole, 1.95 g of potassium carbonate and a few crystals of potassium iodide was stirred at 90° for 8 hrs and overnight at ambient temperature. The reaction mixture was poured into 100 ml of water and extracted with ethyl acetate. The ether extract was dried over anhydrous magnesium sulfate and the solvent was removed in vacuo to yield an oil. The oil was chromatographed on a silica gel (30:1) column using chloroform as the eluent. The solvent was removed in vacuo to yield an oil. The oil was dissolved in ether and ether-hydrogen bromide solution was added dropwise to yield a salt. The salt was recrystallized from methanol-ether to yield product, mp 242°–244°.

ANALYSIS: Calculated for $C_{22}H_{22}N_3O_2F$ HBr: 57.40%C, 5.00%H, 9.14%N; Found: 57.33%C, 5.03%H, 9.11%N.

EXAMPLE 24

3-[1-(6-Fluoro-1,2-benzisoxazol-3-propyl)-4-piperidyl]-5-fluoro-1,2-benzisoxazole hydrochloride A mixture of 6.0 g of 5-fluoro-3-(4-piperidyl)-1,2-benzisoxazole hydrochloride, 7.6 g (80% pure) of 3-(3-chloropropyl)-6-fluoro-1,2-benzisoxazole, 7.5 g of potassium carbonate and 75 ml of dimethylformamide was stirred at 100° for 4 hrs. The cooled mixture was poured into 250 ml water and the aqueous suspension was extracted two times with ethyl acetate. The extract was washed with water, brine and dried over anhydrous magnesium sulfate. The solvent was removed under reduced pressure to give a solid, which was dissolved in ether and converted to a salt with the addition of an ether-hydrogen chloride solution. The salt was recrystallized twice from dimethylformamide-ether to give 3.1 g (31.0%) of product, mp 244°–245°.

ANALYSIS: Calculated for $C_{22}H_{21}F_2N_3O_2$ HCl: 60.89%C, 5.11%H, 9.68%N. Found: 60.52%C, 5.10%H, 9.82%N.

EXAMPLE 25

3-{3-[4-(5-Fluoro-1,2-benzisoxazol-3-yl)piperidyl]-propyl}-2-methylindole

A mixture of 5.0 g of 5-fluoro-3-(4-piperdiyl)-1,2-benzisoxazole hydrochloride, 14.0 g of potassium carbonate, 7.0 g of 2-methyl-3-(3-phenylsulfonylpropyl)indole and 75 ml of dimethylformamide was stirred under nitrogen at 90° for 14 hrs. The reaction mixture was poured into water and extracted with ethyl acetate. The extract was washed with water, brine, dried over anhydrous magnesium sulfate and the solvent was removed in vacuo to give a solid. The solid was triturated with ether and recrystallized twice from ethanol-water to give 3.3 g (43.4%) of product, mp 144°–146°.

ANALYSIS: Calculated for $C_{24}H_{23}FN_3O$: 73.63%C, 6.70%H, 10.73%N; Found: 73.62%C, 6.71%H, 10.84%N.

EXAMPLE 26

3-[1-(6-Fluoro-1,2-benzisoxazol-3-propyl)-4-piperidyl]-6-fluoro-1,2-benzisoxazole hydrochloride A mixture of 2.21 g of 3-(4-piperidyl)-6-fluoro-1,2-benzisoxazole, 6.13 g of sodium bicarbonate, some crystals of potassium iodide and 2.13 g of 3-(3-chloropropyl)-6-fluoro-1,2-benzisoxazole in 20 ml of dimethylformamide was stirred for 2 hrs at 90°–100°. The reaction mixture was filtered and the filter cake was washed with 30 ml of dichloromethane. The solvents were evaporated in vacuo and the residue was dissolved in 30 ml of ethanol and added to 400 ml of half-saturated sodium chloride solution. The precipitate was collected, washed twice with 40 ml water and dried in vacuo over phosphorous pentoxide. The precipitate was triturated with ether-diisopropylether. The precipitate was dissolved in 50 ml of ethanol and 0.7 ml of conc hydrochloric acid was added. After heating to 60°, the solvent was evaporated in vacuo. Benzene (60 ml) was added to the residue and distilled in vacuo. The residue was triturated with ether, filtered and recrystallized from isopropanol-methanolether to give 1.6 g (36.0%) of product, mp 220°.

ANALYSIS: Calculated for $C_{22}H_{21}ClF_2N_3O_2$: 60.89%C, 5.11%H, 9.68%N; Found: 60.33%C, 5.09%H, 9.78%N.

EXAMPLE 27

3-[1-(6-Fluoro-1,2-benzisoxazole-3-propyl)-4-piperidyl]-5-methoxy-1,2-benzisoxazole hydrobromide A mixture of 2.5 g of 5-methoxy-3-(4-piperidyl)-1,2-benzisoxazole hydrochloride, 2.8 g of potassium carbonate, 40 ml of dimethylformamide, a few crystals of potassium iodide and 2.2 g of 3-(3-chloropropyl)-6-fluoro-1,2-benzisoxazole was stirred under nitrogen at 100° for 8 hrs. After cooling to ambient temperature, the reaction mixture was poured into water and the aqueous mixture was extracted with ether (3 times 100 ml). The ether extracts were combined, washed with water and brine and dried over anhydrous magnesium sulfate. Evaporation of the ether under reduced pressure yielded an oil. The oil was chromatographed on a silica gel column (128 g) using dichloromethane-methanol (2%) as eluent to give an oily material. The oily material was dissolved in anhydrous ether and a saturated solution of hydrogen bromide in ether was added to precipitate a salt. Recrystallization of the salt from ethanol yielded 1.8 g (40.7%) of product, mp 192°–194°.

ANALYSIS: Calculated for $C_{23}H_{24}FN_3O_3$ Hbr: 56.33%C, 5.14%H, 8.57%N; Found: 56.39%C, 5.13%H, 8.57%N.

EXAMPLE 28

3-[1-(6-Fluoro-1,2-benzisoxazol-3-propyl)-4-piperidyl]-6-chloro-1,2-benzisoxazole hydrochloride A mixture of 16.5 g of 6-chloro-3-(4-piperidyl)-1,2-benzisoxazole, 17.0 g of 3-(γ-chloropropyl)-6-fluoro-1,2-benzisoxazole, 28.0 g of potassium carbonate, 0.4 g of potassium iodide and 200 ml of dimethylformamide was stirred and heated at 80° for 5 hrs. The reaction mixture was allowed to cool and was filtered. The filtrate was concentrated in vacuo to an oil, which was taken up in 300 ml of ether and washed with an equal portion of brine. The ether layer was dried over anhydrous magnesium sulfate and concentrated in vacuo to give an oil, which solidified upon standing. The solid was dissolved in a minimal amount of ethanol. The ethanol solution was cooled on an ice-bath and 40 ml of ether saturated with hydrogen chloride was added dropwise. The solution was concentrated to 250 ml and cooled on ice. Seeding and addition of 300 ml ether gave salt. Recrystallization of the salt from 2:1 ether-ethanol gave 10.0 g (32%) of product, mp 220°-222°.

ANALYSIS: Calculated for $C_{22}H_{21}ClFN_3O_2$ HCl: 58.68%C, 4.92%H, 9.33%N; Found: 58.84%C, 4.83H, 9.36%N.

EXAMPLE 29

Ethyl (2-methylindol-3-yl)propionate

A mixture of 378 g of phenylhydrazine hydrochloride, 340 g of 4-acetylbutyric acid, 16 ml of conc sulfuric acid and 90 ml of abs ethanol was heated under reflux under a blanket of nitrogen for 5 hrs. The reaction mixture was allowed to cool, poured into 400 ml of water, and the suspension was extracted with 3 300-ml portions of ether. The combined ether extracts were washed with diluted sodium hydroxide solution, water, and the ether layer was dried over anhydrous magnesium sulfate. The mixture was filtered, and the filtrate was evaporated under reduced pressure. Distillation of the residue at 0.15 mm gave 416 g (61%) of product, bp 145°-154°.

EXAMPLE 30

2-Methylindol-3-ylpropanol

A solution of 27.3 g of ethyl (2-methylindol-3-yl)propionate and 100 ml of tetrahydrofuran was added slowly to a suspension of 4.3 g of lithium aluminum hydride and 120 ml of tetrahydrofuran, with stirring. After the addition was complete, the reaction mixture was heated under reflux for 2 hrs, and cooled in an ice bath. Water (17 ml) was added cautiously at ice-bath temperature. The mixture was filtered and the filtrated was concentrated. Distillation of the residue at 0.2 mm gave 15.6 g (68.8%) of product, bp 180°.

EXAMPLE 31

(2-Methylindol-3-yl)propanol phenylsufonate

To a mixture of 143.8 g of (2-methylindol-3-yl)propanol, 100 ml of pyridine and 750 ml of toluene, cooled in an ice-salt bath to 30°, was added dropwise over 20 mins, 116.5 ml of benzenesulfonyl chloride, maintaining the reaction temperature below 7°. The reaction mixture was maintained at about 7° for 1.5 hrs. The ice-salt bath was removed and the mixture was allowed to warm to ambient temperature. After 2.5 hrs, a solution of 72 g of sodium carbonate and 650 ml of water was added. The layers were separated, and the organic layer was washed with a total of 1.2 l of 5% hydrochloric acid in 2 portions. The organic layer was dried over anhydrous potassium carbonate, filtered, and the filtrate was concentrated to about 100 ml under vacuum. Silica gel (Merck, 110 g) was added to the concentrate. After swirling, the mixture was filtered, and the filtrate was evaporated to give 201 g (80.4%) of product.

EXAMPLE 32

4,4-Bis-(4-fluorophenyl)butylchloride

Magnesium metal (98.2 g) was stirred with 100 ml of anhydrous ether under nitrogen for 1 hr. 4-Fluorobromobenzene (700 g) was dissolved in 1750 ml of anhydrous ether. A 20 ml aliquot of the solution was added to the magnesium metal to initiate reaction. Once reflux had begun, the 4-fluorobromobenzene solution was added at such a rate as to maintain a gentle reflux. After the addition was complete, the mixture was heated under reflux for 1 hr. Ethyl cylopropylcarboxylate (180.6 g) was dissolved in 500 ml of anhydrous ether. After the Grignard solution had been cooled to ambient temperature, the solution was added dropwise such that a gentle reflux was maintained. After complete addition of the ester, the mixture was heated under reflux for 45 mins and cooled to ambient temperature. The reaction mixture was quenched with 500 ml of saturated aqueous ammonium chloride and 2 l of ice water. The ether layer was separated and the aqueous layer was extracted twice with ether. The ether extracts were combined and washed with water and saturated brine. The ethereal mixture was dried over sodium sulfate, filtered and the solvent removed under vacuum to provide a quantitative yield or cyclopropyl-bis-(4-fluorophenyl)-methanol.

To a solution of 430 g of cyclopropyl-bis-(4-fluorophenyl)methanol and 875 ml of dry benzene was added dropwise 140 g of thionyl chloride at a rate such that a slow reflux was maintained. When the addition was complete, the mixture was heated at reflux until sulfur dioxide no longer evolved (5 hrs). The benzene was removed under vacuum. Distillation 157°-159° (1.7 mm) proved 300 g (65.4%) of 1,1-bis-(4-fluorophenyl)-3-butenylchloride, bp 157°-159° (1.7 mm).

A suspension of 150 g of 4,4-bis-(4-fluorophenyl-3-butenylchloride, 1 l isopropyl alcohol, and 10 g of 10% palladium-on-charcoal was shaken at room temperature under 40 psi of hydrogen. The uptake of hydrogen ceased after about 5 hrs. The mixture was filtered and the solvent was evaporated to provide an oil. Distillation provided 140.2 g (92.8%) of 4,4-bis-(4-fluorophenyl)butylchloride, bp 155°-158° (1.3 mm).

EXAMPLE 33

3-[1-(6-Fluoro-1,2-benzisoxazol-3-propyl)-4-piperidyl]-5,6-dimethoxy-1,2-benzisoxazole A stirred mixture of 5.0 g of 5,6-dimethoxy-3-(4-piperidyl)-1,2-benzisoxazole, 7.34 g of 3-(3-chloropropyl)-6-fluoro-1,2-benzisoxazole (80% pure), 15.0 g of anhydrous potassium carbonate, 0.25 g of potassium iodide and 120 ml of dimethylformamide was heated at 90° for 6.0 hrs. The cooled mixture was poured into water (400 ml) and extracted with ethyl acetate. The extracts were dried over anhydrous magnesium sulfate and the solvent was removed in vacuo to yield a solid. The solid was purified by passing it through a silica gel column (20:1) and eluting it with dichloromethane-methanol (1%). Recrystallization from ethanol-water gave 2.70 g (32%) of product, mp 149°-151°.

ANALYSIS: Calculated for $C_{24}H_{26}FN_3O_4$: 65.60%C, 5.92%H, 9.57%N; Found: 65.33%C, 5.98%H, 9.26%N.

EXAMPLE 34

3-{3-(4-[5,6-Dimethoxy-1,2-benzisoxazol-3-yl]piperidyl}-2-methyl indole

A stirred mixture of 5.0 g of 5,6-dimethoxy-3-(4-piperidyl)-1,2-benzisoxazole, 6.78 g of 2-methyl-3-(phenylsulfonylpropyl)indole, 120 ml of dimethylformamide and 15.0 g of anhydrous potassium carbonate was heated to 90° for 6 hrs and overnight at ambient temperature. The mixture was poured into water (300 ml) and extracted with ethyl acetate. The extract was dried over anhydrous magnesium sulfate and the solvent was removed in vacuo to yield a solid. The solid was purified by passing it through a silica gel column (20:1) and eluting it with dichloromethane-methanol (1%). Recrystallization two times from ethanol-water yielded 2.0 g (24%) of product, mp 176°–178°.

ANALYSIS: Calculated for $C_{26}H_{31}N_3O_3$: 72.06%C, 7.16%H, 9.70%; Found: 71.85%C, 7.41%H, 8.91%.

EXAMPLE 35

5,6-Dimethoxy-3-{1-[1,3-dihydro-2-oxo-2H-benzimidazole-1-yl-propyl]-4-piperidyl}-1,2-benzisoxazole A stirred mixture of 4.40 g of 5,6-dimethoxy-3-(4-piperidyl-1,2-benzisoxazole, 3.35 g of 1-(3-chloropropyl)-1,3-dihydro-2H-benzimidazole-2-one, 3.56 g of sodium carbonate, 300 ml of 4-methyl-2-pentanone and 0.20 g of potassium iodide was stirred at reflux for 6.0 hrs and stirred overnight at ambient temperature. The reaction mixture was poured into water (300 ml) and extracted with dichloromethane. The extract was dried over anhydrous magnesium sulfate and the solvent was removed in vacuo to yield an oil. The oil was purified by high pressure liquid chromatography (Waters Prep 500; two silica gel columns) using 5% methanol in dichloromethane as the eluent. The free base was dissolved in ether and a saturated hydrogen bromide/ether solution was added dropwise to precipitate the hydrobromide salt. The salt was filtered, washed with ether and recrystallized from toluene/ether to yield 2.50 g (28.1%) of the product, mp 147°–149°.

ANALYSIS: Calculated for $C_{24}H_{28}N_4O_4 \cdot HBr$: 55.72%C, 5.42%H, 10.83%N; Found: 55.51%C, 5.58%H, 10.43%N.

EXAMPLE 36

4-Fluoro-3-{1-[1,3-dihydro-2-oxo-2H-benzimidazole-1-yl-propyl]-4-piperidyl}-1,2-benzisoxazole A mixture of 5.05 g of 4-fluoro-3-(4-piperidyl)-1,2-benzisoxazole hydrochloride, 3.90 g of 1-(3-chloropropyl)1,3-dihydro-2H-benzimidazole-2-one, 100 ml of dimethylformamide, 6.0 g of potassium carbonate and a few crystals of potassium iodide was heated to 90° for 6 hrs and stirred overnight at ambient temperature. The reaction mixture was poured into water and extracted with ethyl acetate. The extract was washed with water, dried over anhydrous magnesium sulfate and the solvent was removed in vacuo to yield a solid. The compound was purified as the free base by filtering it through a silica gel column (10:1) using dichloromethane-methanol (1%) as the eluent. Recrystallization from 2-propanol water gave 2.20 g (26%) of product, mp 174°–175°.

ANALYSIS: Calculated for $C_{22}H_{23}FN_4O_2$: 67.01%C, 5.84%H, 14.21%N; Found: 66.50%C, 5.84%H, 14.07%N.

We claim:

1. A compound of the formula

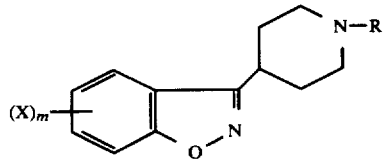

wherein R is a group of the formula

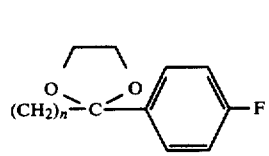

wherein n is 2 or 3; a group of the formula

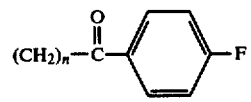

wherein n is 2 or 3; a group of the formula

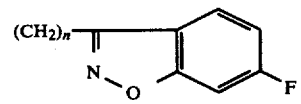

wherein n is 2 or 3; a group of the formula

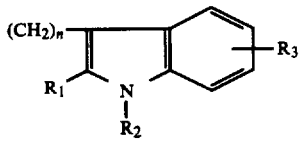

wherein $R_1$ and $R_2$ are each independently hydrogen or loweralkyl, $R_3$ is hydrogen, halogen or loweralkyl and n is 2 or 3; a group of the formula

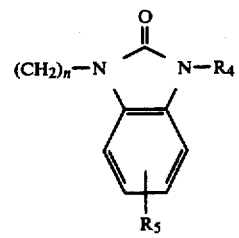

wherein $R_4$ is hydrogen or loweralkyl, $R_5$ is hydrogen, halogen or loweralkyl; and n is 2 or 3; and a group of the formula

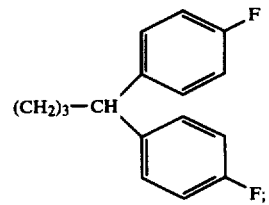

X is hydroen, halogen, loweralkyl, loweralkoxy or hydroxy; and m is 1 or 2; the optical antipodes thereof; or pharmaceutically acceptable acid addition salts thereof.

2. A compound according to claim 1 wherein R is a group of the formula

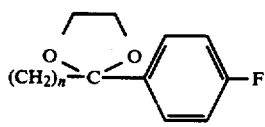

wherein n is 2 or 3.

3. A compound according to claim 2 wherein n is 3.
4. A compound according to claim 1 wherein R is a group of the formula

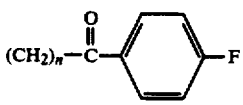

wherein n is 2 or 3.

5. A compound according to claim 4 wherein n is 3.
6. A compound according to claim 1 wherein R is a group of the formula

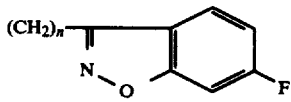

wherein n is 2 or 3.

7. A compound according to claim 6 wherein n is 3.
8. A compound according to claim 1 wherein R is a group of the formula

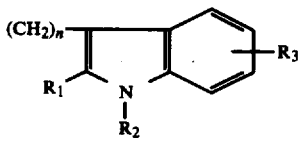

wherein $R_1$ and $R_2$ are each independently hydrogen or loweralkyl, $R_3$ is hydrogen, halogen or loweralkyl, and n is 2 or 3.

9. A compound according to claim 8 wherein $R_1$ is loweralkyl, $R_2$ is hydrogen and n is 3.
10. A compound according to claim 1 wherein R is a group of the formula

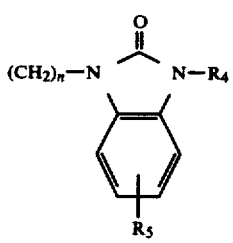

wherein $R_4$ is hydrogen or loweralkyl, $R_5$ is hydrogen, halogen or loweralkyl and n is 2 or 3.

11. A compound according to claim 10 wherein $R_4$ is hydrogen.
12. A compound according to claim 1 wherein R is a group of the formula

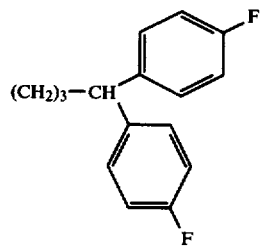

13. The compound of claim 3 which is 3-[1-(4-fluorobenzoylpropyl)-4-piperidyl]-1,2-benzisoxazole ethylene ketal.
14. The compound of claim 3 which is 3-[1-(4-fluorobenzoylpropyl)-4-piperidyl]-6-fluoro-1,2-benzisoxazole ethylene ketal.
15. The compound of claim 3 which is 3-[1-(4-fluorobenzoylpropyl)-4-piperidyl]-6-chloro-1,2-benzisoxazole ethylene ketal.
16. The compound of claim 5 which is 3-[1-(4-fluorobenzoylpropyl)-4-piperidyl]-1,2-benzisoxazole.
17. The compound of claim 5 which is 3-[1-(4-fluorobenzoylpropyl)-4-piperidyl]-6-fluoro-1,2-benzisoxazole.
18. The compound of claim 5 which is 3-[1-(4-fluorobenzoylpropyl)-4-piperidyl]-6-chloro-1,2-benzisoxazole.
19. The compound of claim 7 which is 3-[1-(6-fluoro-1,2-benzisoxazol-3-propyl)-4-piperidyl]-1,2-benzisoxazole.
20. The compound of claim 7 which is 3-[1-(6-fluoro-1,2-benzisoxazol-3-propyl)-4-piperidyl]-5-fluoro-1,2-benzisoxazole.
21. The compound of claim 7 which is 3-[1-(6-fluoro-1,2-benzisoxazol-3-propyl)-4-piperidyl]-6-fluoro-1,2-benzisoxazole.
22. The compound of claim 7 which is 3-[1-(6-fluoro-1,2-benzisoxazol-3-propyl)-4-piperidyl]-5-methoxy-1,2-benzisoxazole.
23. The compound of claim 7 which is 3-[1-(6-fluoro-1,2-benzisoxazol-3-propyl)-4-piperidyl]-6-chloro-1,2-benzisoxazole.
24. The compound of claim 9 which is 3-{3-[4-1,2-benzisoxazol-3-yl)piperidyl]propyl}-2-methylindole.
25. The compound of claim 9 which is 3-{3-[4-(6-fluoro-1,2-benzisoxazol-3-yl)piperidyl]propyl}-2-methylindole.
26. The compound of claim 9 which is 3-{3-[4-(6-chloro-1,2-benzisoxazol-3-yl)piperidyl]propyl}-2-methylindole.
27. The compound of claim 9 which is 3-{3-[4-(5-methoxy-1,2-benzisoxazol-3-yl)piperidyl]propyl}-2-methylindole.
28. The compound of claim 9 which is 3-{3-[4-(5-hydroxy-1,2-benzisoxazol-3-yl)piperidyl]propyl}-2-methylindole.
29. The compound of claim 9 which is 3-{3-[4-(5-fluoro-1,2-benzisoxazol-3-yl)piperidyl]propyl}-2-methylindole.
30. The compound of claim 11 which is 3-{[1,3-dihydro-2-oxo-2H-benzimidizol-1-yl]propyl-4-piperidyl}-1,2-benzisoxazole.
31. The compound of claim 11 which is 3-{1-[1,3-dihydro-2-oxo-2H-benzimidazol-1-yl)ethyl]-4-piperidinyl}-1,2-benzisoxazole.

32. The compound of claim 11 which is 6-chloro-3-{1-[1,3-dihydro-2-oxo-2H-benzimidazol-1-ylpropyl]-4-piperidyl}-1,2-benzisoxazole.

33. The compound of claim 11 which is 6-chloro-3-{1-[1,3-dihydro-2-oxo-2H-benzimidazol-1-ylethyl]-4-piperidyl}-1,2-benzisoxazole.

34. The compound of claim 11 which is 5-fluoro-3-{1-[1,3-dihydro-2-oxo-2H-benzimidazol-1-ylpropyl]-4-piperidyl}-1,2-benzisoxazole.

35. The compound of claim 11 which is 6-fluoro-3-{1-[1,3-dihydro-2-oxo-2H-benzimidazol-1-ylpropyl]-4-piperidyl}-1,2-benzisoxazole.

36. The compound of claim 11 which is 6-methoxy-3-{1-[1,3-dihydro-2-oxo-2H-benzimidazol-1-ylpropyl]-4-piperidyl}-1,2-benzisoxazole.

37. The compound of claim 12 which is 3-{1-[4,4-bis(4-Fluorophenyl)-1-butyl]-4-piperidyl}-1,2-benzisoxazole hydrochloride.

38. The compound of claim 12 which is 3-{1-[4,4-bis(4-fluorophenyl)-1-butyl]-4-piperidyl}-6-fluoro-1,2-benzisoxazole.

39. The compound of claim 12 which is 3-{1-[4,4-bis(4-fluorophenyl)-1-butyl]-4-piperidyl}-5-fluoro-1,2-benzisoxazole.

40. The compound of claim 12 which is 3-{1-[4,4-bis(4-fluorophenyl)-1-butyl]-4-piperidyl}-5-methoxy-1,2-benzisoxazole.

41. The compound of claim 12 which is 3-{1-[4,4-bis(4-fluorophenyl)-1-butyl]-4-piperidyl}-5-hydroxy-1,2-benzisoxazole.

42. The compound of claim 12 which is 6-chloro-3-{1-[4,4-bis(4-fluorophenyl)-1-butyl]-4-piperidyl}-1,2-benzisoxable.

43. The compound of claim 12 which is 5,6-dimethoxy-3-{1-[4,4-bis(4-fluorophenyl)-1-butyl]-4-piperidyl}-5-methoxy-1,2-benzisoxazole.

44. The compound of claim 7 which is 3-[1-(6-fluoro-1,2-benzisoxazol-3-propyl)-4-piperidyl]-5,6-dimethoxy-1,2-benzisoxazole.

45. The compound of claim 9 which is 3-{3-(4-[5,6-dimethoxy-1,2-benzisoxazol-3-yl]piperidyl)propyl}-2-methyl indole.

46. The compound of claim 11 which is 5,6-dimethoxy-3-{1-[1,3-dihydro-2-oxo-2H-benzimidazole-1-ylpropyl]-4-piperidinyl}-1,2-benzisoxazole hydrobromide.

47. The compound of claim 11 which is 4-fluoro-3-{[1,3-dihydro-2-oxo-2H-benzimidazole-1-yl-propyl]-4-piperdinyl}-1,2-benzisoxazole.

48. A method of treating psychoses comprising administering to a mammal in need of psychoses treatment a psychoses-treating, effective amount of a compound as defined in claim 1.

49. A psychoses-treating composition comprising an inert psychoses-treating adjuvant and, as the active ingredient, an amount effective in treating psychoses of a compound as defined in claim 1.

* * * * *

UNITED STATES PATENT AND TRADEMARK OFFICE
CERTIFICATE OF CORRECTION

PATENT NO. : 4,352,811

DATED : October 5, 1982

INVENTOR(S) : Joseph T. Strupczewski; Richard C. Allen

It is certified that error appears in the above-identified patent and that said Letters Patent is hereby corrected as shown below:

Column 9     Line 2

"does"     should be     -- dose --

Column 8     Line 21

"sysnthesis"     should be     -- synthesis --

Column 9     Line 27

"4-piperidyl)-1"     should be -- 4-piperidyl-1 --

Column 9     Line 46

"3-dihdro"     should be     -- 3-dihydro --

Column 12     Line 34

"1-(4-Fluorbenzoyl..."     should be     -- 1-(4-Fluorobenzoyl --

Column 14     Line 39

"sautrated"     should be     -- saturated --

Column 14     Line 52     Example 5

"piperidyl]"     should be     -- piperidyl) --

"benzisoxable"     should be -- benzisoxazole --

UNITED STATES PATENT AND TRADEMARK OFFICE
CERTIFICATE OF CORRECTION

PATENT NO. : 4,352,811

DATED : October 5, 1982

INVENTOR(S) : Joseph T. Strupczewski; Richard C. Allen

Page 2 of 3

It is certified that error appears in the above-identified patent and that said Letters Patent is hereby corrected as shown below:

Column 16   Line 28   Example 9

"(13% yield)"   should be   -- (31% yield) --

Column 17   Line 56   Example 13

"anlytical"   should be   -- analytical --

Column 18   Line 22   Example 15

"3-{3-]4"   should be   -- 3- 3-[4 --

Column 18   Line 67   Example 17

"4.06 g"   should be   -- 4.60 g --

Column 21   Line 49   Example 25

"piperdiyl"   should be   -- piperidyl --

Column 23   Line 4   Example 28

"$C_2 2H..$"   should be   -- $C_{22}H$ --

Column 24   Line 1   Example 32

"cylopro..."   should be   -- cyclopro... --

UNITED STATES PATENT AND TRADEMARK OFFICE
CERTIFICATE OF CORRECTION

PATENT NO. : 4,352,811
DATED : October 5, 1982
INVENTOR(S) : Joseph T. Strupczewski; Richard C. Allen It is certified that error appears in the above-identified patent and that said Letters Patent is hereby corrected as shown below:

Column 25    Line 6    Example 34

"9.70%"    should be    -- 9.70%N --

Column 18    Line 41    Example 16

"benzmidazol"    should be -- benzimidazol --

Column 26    Line 64

"hydroen"    should be    -- hydrogen --

Signed and Sealed this

Fifteenth Day of March 1983

[SEAL]

Attest:

GERALD J. MOSSINGHOFF

Attesting Officer    Commissioner of Patents and Trademarks